United States Patent [19]

Costanzi et al.

[11] Patent Number: 4,946,880

[45] Date of Patent: Aug. 7, 1990

[54] SILYLATED U.V. STABILIZERS CONTAINING HINDERED TERTIARY AMINES

[75] Inventors: Silvestro Costanzi; Damiano Gussoni, both of Milan; Omero Zavattini, deceased, late of Curtatone; by Clara Pungiluppi, heir; by Renato Zavattini, heir, both of Mantova; Luciano Pallini, Parma, all of Italy

[73] Assignee: Enichem Synthesis S.p.A., Palermo, Italy

[21] Appl. No.: 103,961

[22] Filed: Oct. 5, 1987

[30] Foreign Application Priority Data

Oct. 8, 1986 [IT] Italy ................................ 21935 A/86

[51] Int. Cl.$^5$ ................. C08K 5/3435; C08K 5/3477; C08K 5/357
[52] U.S. Cl. .......................................... 524/96; 524/99; 524/104; 544/106; 544/171; 544/177; 546/14; 548/406; 428/441; 428/451; 428/523; 526/265; 528/28; 528/38; 528/14; 528/18; 528/32
[58] Field of Search ............................ 524/99, 96, 104; 526/265; 546/14; 544/106, 171, 177; 548/406; 528/14, 18, 32, 28, 38

[56] References Cited

U.S. PATENT DOCUMENTS 4,210,578  7/1980  Rody et al. .......................... 546/14

FOREIGN PATENT DOCUMENTS 0182415  5/1986  European Pat. Off. ............. 546/14
0626092  9/1978  U.S.S.R. ................................ 546/14
0758168 10/1956  United Kingdom .................. 546/14

Primary Examiner—Kriellion Morgan
Attorney, Agent, or Firm—Hedman, Gibson, Costigan, & Hoare

[57] ABSTRACT

Reactive stabilizer compounds, to be used in the stabilization of organic polymers, contain a sterically hindered, N-substituted piperidinic, morpholinic or pyrrolidinic group, and at least a hydrolysable silicic function.

Such compounds give rise, by hydrolysis of the silicic function, to complex resinous structures endowed with stabilizing properties.

The reactive stabilizer compounds can spontaneously hydrolyse inside the polymer, or they can be stably supported on a solid support, or they can be chemically linked to the polymeric chain to be stabilized.

21 Claims, No Drawings

SILYLATED U.V. STABILIZERS CONTAINING HINDERED TERTIARY AMINES

The present invention relates to reactive stabilizer compounds, suitable for use in the stabilization of organic polymers, and in the preparation of top-coatings, containing in their molecule a sterically hindered tertiary aminic group, and at least one hydrolysable silicic function.

The present invention relates also to the stabilized polymeric compositions, and to the process for the preparation of said reactive stabilizer compounds, and of the stabilized polymeric compositions.

It is known that the organic polymers, such as, e.g., the polyolefins, undergo degradation over time due to the exposure to the atmospheric agents and, above all, to U.V. light, and furthermore easily suffer thermooxidative degradations during the processing and transformation steps.

The most evident symptoms of these degradations are, e.g., the decrease in polymer tensile strength and flexibility, accompanied by the change in melt flow index and in polymer melt flow time, and the alterations in the optical properties of the manufactured article. In order to prevent such degradation of the polymeric material, in the polymers antioxidants and/or stabilizer compounds are usually introduced, which are, generally, sterically hindered phenols, or benzotriazoles, phosphorus compounds, particular nickel complexes, sterically hindered amines.

Among the sterically hindered amines, pirrolidine derivatives (U.S. Pat. Nos. 4,325,864 and 4,346,188), and several organic compounds containing in their molecule at least a tetramethylmorpholine moiety (U.S. Pat. No. 4,617,333) are known.

Some derivatives of pyrrolidine, morpholine and piperidine, containing in their molecule also a hydrolysable silylated function are also known.

Such silylated amines, although secure a good stability of the polymer to U.V. light and to the oxidation caused by atmospheric agents, eliminate only partially the thermooxidative liability of the polymeric materials, which appears during the operations of transformation and processing of said polymers.

Besides the problem due to such thermooxidative liability, which can lead to an even very deep degradation of the treated polymeric material, the main technical problems to be faced in the stabilization of the organic polymers derive from the need of using stabilizer agents which are compatible with the polymeric matrix and which, once incorporated, are no longer liable to extraction from it.

The stabilizers known from the prior art did not demonstrate to be completely satisfactory from all of these viewpoints.

The present Applicant has found now that it is possible to overcome the drawbacks deriving from the present state of the art, by using reactive stabilizer compounds containing in their molecule a sterically hindered, N-substituted pyrrolidinic, morpholinic or piperidinic group, and at least a hydrolysable silicic function.

Such stabilizers, besides securing a high stability of the polymer to U.V. light and to the atmospheric agents, minimize the thermooxidative lability of the same polymers.

Such reactive stabilizer compounds give rise, thanks to the presence of the hydrolysable silicic functions, to complex resinous structures endowed with characteristics of compatibility with the organic polymers, and of non-extractability from them, which are higher than those of the stabilizers known from the prior art.

Therefore, such reactive stabilizers are a purpose of the present invention.

A further purpose of the present invention are the processes for the preparation of said reactive stabilizer compounds.

Also another purpose of the present invention are the polymeric compositions stabilized by means of the transformation products, at their silicic function, of said reactive stabilizer compounds.

Still another purpose of the present invention are the processes for the preparation of said stabilized polymeric compositions.

In particular, according to the present invention, the reactive stabilizer compounds are characterized in that they contain, in their molecule, the 2,2,6,6-tetramethylpiperidine group:

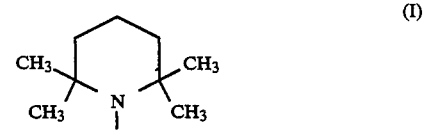
(I)

or the 2,2,6,6-tetramethylmorpholine group:

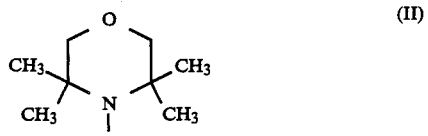
(II)

or the 2,2,5,5-tetramethylpyrrolidine group:

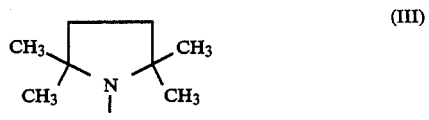
(III)

wherein said groups bear at least one silicic function, hydrolysable to a silanol group, linked to (I), (II) and (III) through a silicon-carbon bond.

More particularly, the reactive stabilizer compounds of the present invention can belong to the following compound classes:

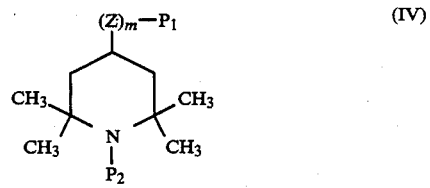
(IV)

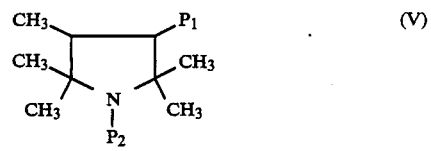
(V)

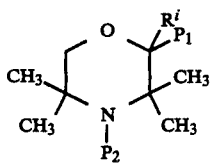  (VI)

wherein:
m is 0 or 1;
$R^i$ is hydrogen or methyl;
Z is a group selected from

(wherein $R^{ii}$ is a straight or branched alkyl radical, containing from 1 to 5 carbon atoms);
wherein at least one from $P_1$ and $P_2$ is a radical having the formula:

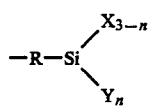  (VII)

wherein: n=1, 2 or 3;
R is a straight or branched alkylenic radical containing from 1 to 10 carbon atoms, or can be represented by:

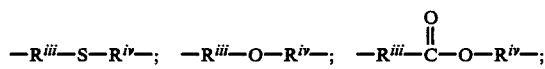

(wherein $R^{iii}$ and $R^{iv}$ are straight or branched alkylene radicals, containing from 2 to 10 carbon atoms in all);
X is a straight or branched alkyl radical of from 1 to 5 carbon atoms;
Y is hydrogen, halogen, acyl-($C_{1-4}$)-oxy, alkyl-($C_{1-4}$)-oxy, amino, amino-oxy or silyl-oxy; and the other one from $P_1$ and $P_2$ is: p1 (a) a straight or branched alkyl radical of from 1 to 10 carbon atoms;
(b) a phenyl or cycloaliphatic, alkyl-phenyl or alkyl-cycloaliphatic radical.

Specific examples of reactive stabilizer compounds within the scope of formulae (IV), (V) and (VI) are the following:

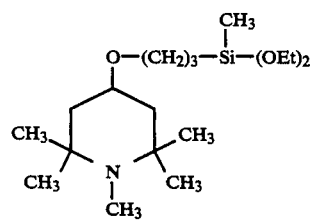  (VIII)

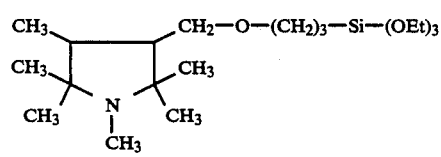  (IX)

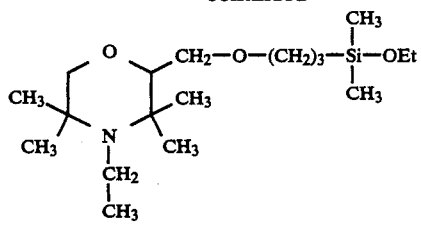  (X)

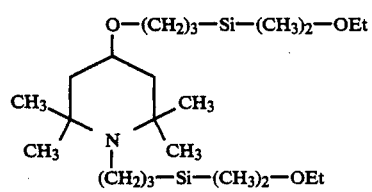  (XI)

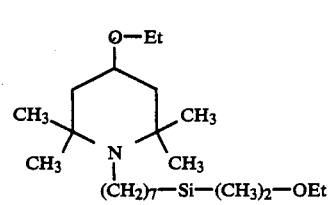  (XII)

The reactive stabilizer compounds (VIII), (IX), (X) can be obtained by starting from the corresponding allyl-derivatives:

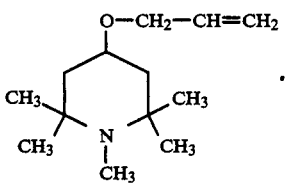  (XIII)

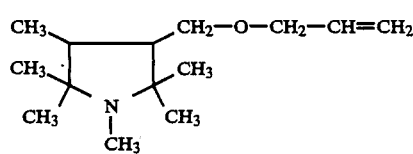  (XIV)

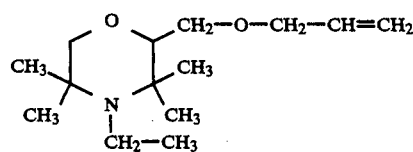  (XV)

by silylation with, respectively, methyl-diethoxy-silane, triethoxy-silane and dimethyl-ethoxy-silane; and compounds (XI) and (XII) can be obtained analogously to the preceding ones, by starting from the corresponding compounds also allylated on their nitrogen atoms:

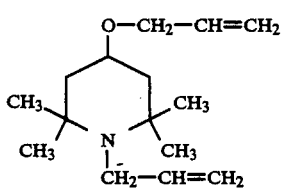  (XVI)

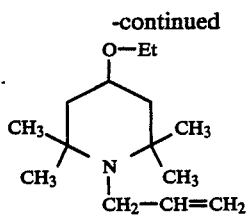

(XVII)

The compounds (XVI) and (XVII) can be prepared in their turn from the corresponding amines by reaction with allyl carbonate, according to as disclosed in another Italian patent application in the same Applicant's name.

In general, the reactive stabilizer compounds of the present invention can be prepared by silylating a 2,2,6,6-tetramethyl-piperidine, or a 2,2,6,6-tetramethyl-morpholine, or a 2,2,3,5,5-pentamethyl-pyrrolidine, bearing on their ring a group having an alkylenic unsaturation, preferably in a terminal position.

A class of silylating agents suitable for the intended purpose can be defined by the general formula:

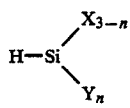

(XVIII)

wherein X, Y and n have the above reported meaning.

Specific examples of silylating agents complying with formula (XVIII) are the following:

H Si (CH$_3$) Cl;
H Si (CH$_3$) Cl$_2$;
H Si Cl$_3$;
H Si (CH$_3$) (OCH$_3$)$_2$;
H Si (CH$_3$) (OC$_2$H$_5$)$_2$;
H Si (OC$_2$H$_5$)$_3$;
H$_2$Si (C$_2$H$_5$)$_2$;
H Si (OCH$_3$)$_3$;
H Si (CH$_3$)$_2$ O Si (CH$_3$)$_2$H;
H Si (CH$_3$)$_2$ O Si (CH$_3$)(OCH$_3$)$_2$;
H Si (CH$_3$)$_2$ O NO (CH$_3$)$_2$;
H Si (CH$_3$)$_2$ N(CH$_3$)$_2$;
H Si (CH$_3$) (O CO CH$_3$)$_2$;
H Si (CH$_3$)[O NO (CH$_3$)$_2$]$_2$;

The silylation reaction is suitably carried out at a temperature comprised within the range of from 0° to 200° C., preferably of from room temperature (20°–25° C.) to 120° C., with reactant amounts ranging from the stoichiometric amounts to an excess of the silylating agent. Said excess may usually reach 20% on a molar basis. However, in case of use of disilanes, a large excess of the silylating agent, of, e.g., up to 10 times the stoichiometric amount, can be suitably used.

The silylation reaction is catalyzed by metal catalysts, U.V. light and free-radical initiators. The preferred catalysts are the platinum compounds, and the platinum complexes with olephins, in particular, chloroplatinic acid. In case of platinum-based catalysts, the concentration of the catalyst, computed as the metal, can be comprised within the range of from 1 to 200 parts per million, and preferably of from 5 to 50 parts per million in the reaction medium.

The silylation reaction can be carried out in an inert (non-reactive) organic solvent, usually selected from the aliphatic hydrocarbons, cycloaliphatic hydrocarbons and aromatic hydrocarbons, and ethers, which are liquid under the operating conditions. Examples of solvents suitable for the intended purpose are heptane, cyclohexane, toluene, tetrahydrofuran, dioxane and dimethoxy-ethane.

The reaction times are a function of the particular reactants used and of the reaction temperature, and are usually comprised within the range of from 0.5 to 10 hours.

At the end of the silylation reaction, the possibly used solvent, and the possible excess of silylating agent are stripped off, and the reactive stabilizer compound is recovered from the residue of said stripping by means of usual techniques, such a crystallization and vacuum-distillation.

However, in general, the high values of yield and of selectivity of the silylation reaction render the treatments of separation or purification of the desired end product unnecessary.

Another class of silylating agents suitable for the intended purpose can be defined by the general formula:

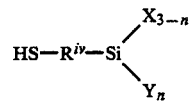

(XIX)

wherein R$^{iv}$, X, Y and n have the above indicated meaning.

Specific examples of silylating agents which fall within the scope of formula (XIX) are γ-mercapto-propyl-tri-alkoxy-silanes, in particular γ-mercapto-propyl-tri-methoxy-silane.

In case of use of silylating compounds falling within the scope of formula (XIX), the reaction can be carried out under the general silylating conditions as previously disclosed, in the presence of catalysts of free-radical or ionic type, or under the action of U.V. light. In this case, the preferred catalysts are the azo-compounds, e.g., azo-bis-isobutyronitrile, which are suitably used in an amount of from 0.1 to 10% by weight, and, preferably, of from 0.5 to 2% by weight in the reaction medium.

The reactive stabilizer compounds of the present invention undergo the hydrolysis, under mild conditions, at their silyl function, generating silanol groups, which condense with each other, generating complex resinous structures endowed with stabilizing properties.

The hydrolysis at the silyl function takes place by the simple contact with water, or with the environmental humidity, at room temperatures (20°–25° C.), or at lower than room temperatures.

The mutual condensation of the sylanol groups, to yield the complex resinous structures, can be favoured by acidic or basic agents, by metal soaps and esters, or by organometallic compounds, in particular of zinc, lead and tin.

Suitable catalysts for the intended purpose are zinc octanoate, lead naphthenate and tin dibutyl-laurate. The amount of catalyst can be comprised within the range of from 0,1 to 10% by weight, and preferably of from 0.2 to 3% by weight, relatively to the reactive stabilizer compound undergoing the resinification. Said resinification reaction can be carried out at room temperature (20°–25° C.), or also at higher or lower than room temperatures.

The so-obtained complex resinous structure can be added to the organic polymer to be stabilized by means of the usual techniques used for the intended purpose.

According to another form of practical embodiment of the present invention, the reactive stabilizer compounds are directly added to the organic polymer, inside which the reactions of hydrolysis of the silicic function and of interaction between the silanol groups spontaneously occur, thus the stabilized polymeric composition being obtained.

According to a further form of practical embodiment of the present invention, the hydrolysis at the silicic function of the reactive stabilizer compounds, and a partial resinification of the so-obtained hydrolysis products are carried out outside the polymer. The product from the partial resinification is then introduced in the organic polymer to be stabilized, inside which the completion of the resinification occurs.

According to a preferred form of practical embodiment of the present invention, the reactive stabilizer compounds of the invention are converted into a pigment form and, as such, they are added to the organic polymer to be stabilized. For that purpose, the reactive stabilizer compounds are hydrolysed and resinified by exposure to moisture, optionally in the presence of a catalyst selected from those previously disclosed. The so-obtained resinification products, which have the form of glassy solids, still soluble in the aliphatic alcohols, are heated to temperatures higher than 100° C., and generally comprised within the range of from 120° to 220° C., for a time of from 10 minutes to 6 hours. After cooling, the solid is ground and powdered, and the so-obtained powder is added to the polymer to be stabilized.

According to a further form of practical embodiment of the present invention, the reactive stabilizer compounds are added to silicone paints, such as those available from the market, in general in a hydrocarbon vehicle, and are co-resinified together with said paints, by adopting the thermal treatments typical for such paints. The resulting glassy products are ground and powdered and the powder is added to the organic product to be stabilized. According to this latter form of practical embodiment, an amount of reactive stabilizer compound of from 10 to 90% by weight, relatively to the silicone paint, can be used.

In any case, the powders which are added to the polymer to be stabilized should suitably have particle sizes smaller than 10 microns, and preferably of the order of from 0.5 to 2 microns.

The structure of the products from the resinification reaction depends basically from the number of the hydrolysable groups linked to the silicic function of the reactive stabilizer compounds, and from the number of silicic functions present in the starting compound.

For example, in case of compound (X), which contains only one silicic function per molecule, and only one hydrolysable group, the reactions of hydrolysis and resinification proceed until a dimer is produced, which can be defined, in the present case, by means of the following formula:

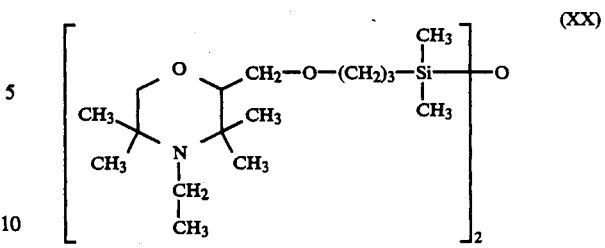

On the contrary, in case of compounds containing two silicic functions with only one hydrolysable group, linear resinous structures can be obtained, an example of which is:

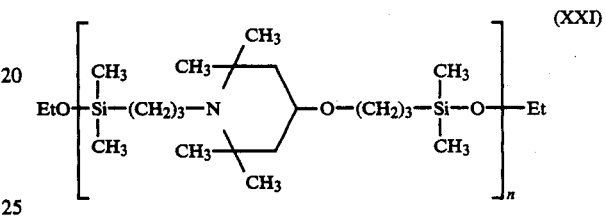

If, on the contrary, compounds are used, which contain a silicic function, with 2 or 3 hydrolysable groups, more complex resinification products are obtained, which are constituted by branched, or tridimensional chains.

The reactive stabilizer compounds according to the present invention can also be fixed onto a solid support containing surface hydroxy groups. Suitable supports for said purpose are siliceous materials of either natural or synthetic origin, such as diatomaceous earth, celite, silica gel, cement, glass, silico-aluminates in general.

Among all of these supports, that type of silica which is known as fumed silica is preferred, which, together with good optical characteristics, shows a low bulk density, a large surface area (generally larger than 200 m$^2$/g), and a high surface concentration of hydroxy groups.

The bonding to the support takes place by the reaction of the reactive stabilizer compound, in its hydrolysed form, with the surface hydroxy groups of the support. In practice, the support, in the form of powders or granules, is contacted with a solution of the reactive stabilizer compound, in an inert organic solvent, such as an aliphatic, cycloaliphatic or aromatic hydrocarbon, or an ether. The process is furthermore carried out in the liquid phase, at a temperature comprised within the range of from room temperature (20°-25° C.) up to approximately 100° C. The hydrolysis of the reactive stabilizer compound, and its bonding to the support is obtained within a time of the order of from 0.5 to 10 hours.

The so-supported stabilizer is added to the organic polymer undergoing the stabilization, by means of the usual techniques. This form of practical embodiment supplies the additional advantage of an optimum distribution of the stabilizer inside the polymer.

According to a further form of practical embodiment of the present invention, the reactive stabilizer compounds of the invention are chemically linked to the organic polymer to be stabilized. This technique is particularly efficacious in case of low-molecular-weight diolephinic polymers or copolymers. The reaction between the reactive stabilizer compound and the polymer takes generally place at temperatures comprised within the range of from room temperatures (20°–25° C.) up to approximately 100° C., in the presence of an inert diluent, within a time of from 0.5 to 10 hours.

The reactive stabilizer compounds of the present invention can be added to the organic polymers in general, and, in particular, to the homopolymers and copolymers of olephins and diolephins, such as polypropylene, polybutadiene and high- and low-density polyethylene.

The stabilized polymeric compositions of the present invention contain a stabilizing amount of the hereinabove disclosed stabilizer compounds. In particular, the stabilizing amount of said compounds is that amount which supplies the composition with at least 0.003% of active nitrogen, wherein by "active nitrogen", the nitrogen of the piperidine, morpholinic or pyrrolidinic ring is meant.

The upper limit of the amount of stabilizer present in the composition is not critical, however not exceeding 0.03% by weight of active nitrogen is preferred, both due to cost reasons, and in order not to cause undesired changes in one or more characteristic(s) of the organic polymer.

In the preferred form of practical embodiment, the polymeric compositions of the present invention contain an amount of active nitrogen of from 0.005 to 0.02% by weight, with preferred amounts being of from 0.010 to 0.015% by weight.

The following experimental examples are supplied for merely illustrative purposes, and they should not be construed as being limitative of the scope of the invention.

EXAMPLE 1

Preparation of 1,2,2,6,6-pentamethyl-4-(2-propenyloxy)-piperidine

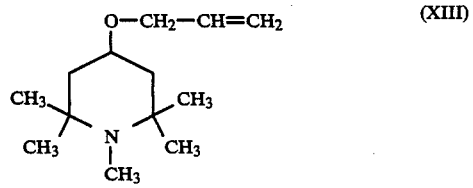

(XIII)

105.5 g (0.5 mol) of 2,2,6,6-tetramethyl-4-(2-propenyloxy)-piperidine prepared as disclosed in Example 3, is dissolved in 200 ml of heptane.

To this solution, 30 g of NaOH powder is added, and 85.2 g (0.6 mol) of $CH_3I$ is added dropwise, over a 2-hour time, making sure that the temperature remains around 40° C.

At the end of the addition of $CH_3I$, the temperature is increased to 85° C., and the mixture is maintained stirred at this temperatures 4 hours long.

At the end of this time, the solution is washed with two portions, of 100 ml each, of $H_2O$, the aqueous phase is separated, and the organic phase is distilled.

Product (XIII) has a boiling temperature of approximately 116°–118° C. (under 12 $mm_{Hg}$) and is obtained with a yield of 80%.

The structure of compound (XIII) is confirmed by the elemental analysis, and by the data from IR, NMR, mass spectrometry.

| Elemental Analysis: | | | |
|---|---|---|---|
| % experimental | C 73 | H 12.1 | N 6.8 |
| % theoretical | C 73.9 | H 11.8 | N 6.6 |

EXAMPLE 2

Preparation of N-(2-propenyl)-2,2,6,6-tetramethyl-4-piperidinol

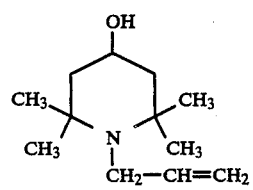

(XXII)

To an autoclave of 250 ml of capacity, equipped with stirring means, 25 g (0.16 mol) of 2,2,6,6-tetramethylpiperidinol and 49 g (0.4 mol) of allyl bromide are charged.

The temperature is increased to 120° C., and the reaction is allowed to proceed at this temperature for a 5-hour time.

During the reaction, piperidinol hydrobromide is formed as a byproduct.

At the end of this reaction time, the mixture is cooled to room temperature, 150 ml of water and 100 ml of ethyl ether are added. The organic phase is separated, and is washed again with 50 ml of water.

After this washing, the organic phase is distilled to remove the solvent.

The organic residue is crystallized from hexane. The crystallization suspension if filtered, and the precipitate is dried; 14.5 g of product (XXII) is obtained (yield of 47%), whose melting point is 86°–88° C.

The structure of compound (XXII) is confirmed by the elemental analysis, and by the data from IR and NMR spectrometry.

| Elemental Analysis: | | | |
|---|---|---|---|
| % experimental | C 72.9 | H 11.9 | N 7.0 |
| % theoretical | C 73.1 | H 11.7 | N 7.1 |

EXAMPLE 3

Preparation of Compound (XXIII)

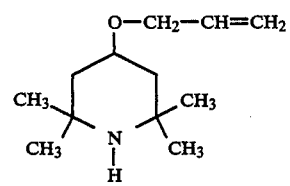

(XXIII)

To a four-neck flask, equipped with stirring means, thermometer, dropping funnel and reflux condenser, 200 ml of dimethoxy-ethane, 47.1 g (22.6 mmol) of tetramethylpiperidinol and 13 g (0.325 mol) of potassium metal are charged under a stream of anhydrous nitrogen.

With stirring, the suspension is mildly refluxed for 6 hours. At the end of this time, not all potassium has reacted. The reaction mixture is cooled to 50° C., and through the dropping funnel 28.6 ml (0.33 mol) of allyl bromide is slowly added, with the temperature being maintained within the range of from 50° to 60° C. After the completion of the addition, the mass is maintained under slowly boiling conditions 30 minutes long. A white precipitate of potassium bromide is formed, which is maintained in suspension. At the end of said time, a small aliquot of methanol (5 ml) is added, to remove any unreacted potassium metal possibly present.

After cooling, the suspension is filtered through a sintered glass septum, and potassium bromide is washed with three aliquots of 50 ml of dimethoxy-ethane.

The liquid cuts from the washes and the filtrate are combined, and submitted to fractional distillation under vacuum (1 mm$_{Hg}$). 40.5 g is obtained of compound (XXIII), equivalent to a yield of 68.5%.

The so obtained product (XXIII) has a boiling point of 56°-58° C.

| Elemental Analysis: | | | |
|---|---|---|---|
| % theoretical | C 73.1 | H 11.7 | N 7.1 |
| % found: | C 73.0 | H 11.5 | N 7.0 |

EXAMPLE 4

Preparation of Compound (XVI)

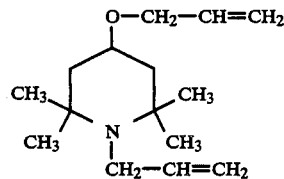

(XVI)

To a 3-neck flask of 500 ml of capacity, equipped with thermometer and refluxing condenser, 150 g (0.76 mol) of propenyloxy-piperidine, prepared as reported in Example 3, 115 g (0.81 mol) of bis-allyl-carbonate and 1.35 g (7.6 mmol) of PdCl is added, working under an inert gas atmosphere.

The solution is heated to 110° C. and the reaction is allowed to proceed, with stirring, for 24 hours.

At the end of this time, the reaction mixture is distilled, and product (XVI) is thus obtained, with a boiling point of 92°-93° C. (under 0.4 mm$_{Hg}$), with a yield of 85%.

From the elemental analysis, the following data is obtained:

| % theoretical | C 75.9 | H 11.4 | N 5.9 |
|---|---|---|---|
| % experimental | C 76.1 | H 11.3 | N 6.1 |

EXAMPLE 5

Preparation of N-(β-hydroxyethyl)-2,2,6,6-tetramethyl-4-(2-propenyloxy)-piperidine

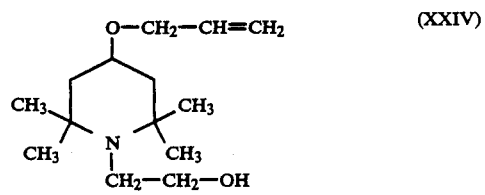

(XXIV)

To an autoclave equipped with magnetic-driven stirring means, 19.7 g (0.1 mol) of 4-allyloxytetramethyl-piperidine and 8 g (0.18 mol) of ethylene oxide are charged.

The autoclave is heated to 90°-95° C., and the reaction is made proceed for 5 hours. At the end of this time, the temperature is reduced back to room values, hexane is added and the reaction mixture is washed with 2 portions, of 20 ml each, of H$_2$O.

The organic phase is separated, and the solvent is distilled. 23.2 g is obtained of product (XXIV) (yield of 96%). The results of the elemental analysis are the following:

| % theoretical | C 69.7 | H 11.2 | N 5.8 |
|---|---|---|---|
| % experimental | C 70.1 | H 11.2 | N 6 |

EXAMPLE 6

Preparation of Compound (XXV)

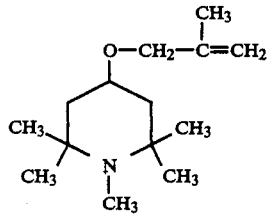

(XXV)

To a flask of 250 ml of capacity, equipped with stirring means, reflux condenser and thermometer, 85.5 g (0.5 mol) of 1,2,2,6,6-pentamethyl-piperidinol is charged.

0.3.10$^{-3}$ mol of tetrabutyl-ammonium bromide and 120 g (1.33 mol) of metallyl chloride are added.

The reaction is made proceed 5 hours long, under refluxing conditions.

At the end of this time period, the reaction mixture is treated with 200 ml of water and 200 ml of toluene. The two phases are separated, and the organic phase is washed again with 50 ml of water.

The organic phase is separated and distilled.

The product (XXV), which has a boiling point of 105°-107° C. (under 10 mm$_{Hg}$), is obtained with a yield of 94%.

The structure of the product is confirmed by the data of IR, NMR and mass spectra. The elemental analysis supplies the following results:

| % experimental | C 75 | H 11.8 | N 6.1 |
|---|---|---|---|

| % theoretical | C 74.7 | H 12.0 | N 6.2 |
|---|---|---|---|

EXAMPLE 7

Preparation of Compound (XXVI)

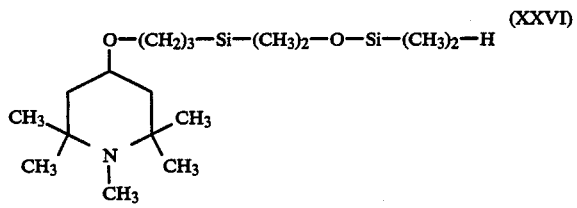

21.1 g (0.1 mol) of 1,2,2,5,5-pentamethyl-4-(2-propenyloxy)-piperidine (prepared as disclosed in Example 1) is reacted with 86 ml (0.5 mol) of tetramethyldisiloxane, in the presence of 1 ml of solution at 2% by weight of $H_2PtCl_6.6H_2O$ in isopropanol. The reaction mixture is heated to the temperature of 80° C., for a 4-hour time. At the end of this time, the reaction mixture is distilled.

The compound (XXVI), which has a boiling temperature of 120°–125° C. (under 0.2 $mm_{Hg}$) is obtained with a yield of 90%.

The product is a viscous, colourless liquid and its IR spectrum shows a band at 2120 cm$^{-1}$, attributable to the Si—H bond.

EXAMPLE 8

Grafting of Product (XXVI) on liquid polybutadiene

To 24 g (0.01 mol) of a commercial polybutadiene having a molecular weight of 2400 and a vinyl group content of 18.7%, 0.03 mol of compound (XXVI), prepared as disclosed in Example 7, dissolved in 100 ml of cyclohexane is added.

The mixture is heated to 100° C. for 6 hours, with no catalyst added. At the end of this time, the solvent is removed, and the so-obtained polymer shows an IR spectrum with no relevant bands for Si—H and

bonds.

EXAMPLE 9

Preparation of Compound (XIV)

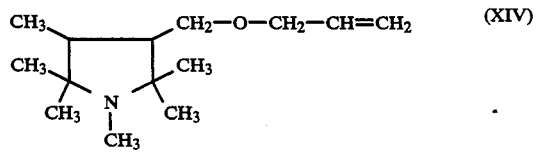

1,2,2,3,5,5-Hexamethyl-4-methylol-pirrolidine (3.4 g; 18.4 mmol) is reacted with 0.88 g of potassium metal (22.0 mmol) in dimethoxyethane (50 ml) under refluxing conditions for 10 hours.

At the end of this time, unaltered potassium is still present.

The reaction mixture is cooled to 60° C. and, with precaution, 2.1 ml of allyl chloride (25.6 mmol) is added within approximately 5 minutes. After a 1-hour reaction at 60° C., a suspension is obtained, which is filtered through sintered glass, dimethoxyethane is evaporated off under reduced pressure at room temperature, and the residual oil is distilled under reduced pressure to yield compound (XVI) having a boiling point of 91°–93° C. (under 2 $mm_{Hg}$). The structure of compound (XIV) is confirmed by mass spectroscopy, IR and HNMR analysis, and by the elemental analysis.

EXAMPLE 10

Preparation of Compound (IX)

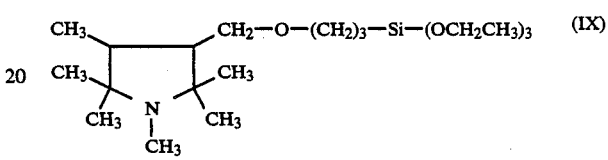

12.7 mol of compound (XIV) is reacted at 135° C. with 2.8 ml of triethoxysilane (15.0 mmmol) for 4 hours, in the presence of 10 µl of a solution at 2% by weight of $H_2PtCl_6.6H_2O$ in isopropanol.

At the end of the reaction, the resulting oil is distilled, to obtain a cut having a boiling point of 140°–149° C. (under 0.5 $mm_{Hg}$) of compound (IX) (Yield 75%). The structure of compound (IX) is confirmed by mass spectroscopy, IR and $^1$HNMR analysis, and by the elemental analysis.

EXAMPLE 11

Preparation of Compound (VIII)

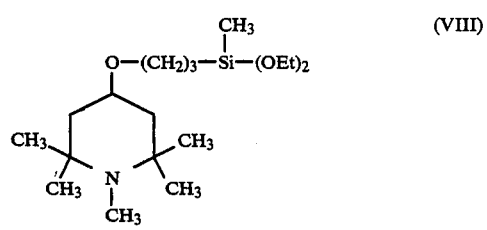

To a flask of 200 ml of capacity, equipped with thermometer, dropping fummel and bubble condenser, 70 g (0.33 mol) of 1,2,2,6,6-pentamethyl)-4-(2-propenyloxy)-piperidine, prepared as disclosed in Example 1, and 0.1 ml of a solution of $H_2PtCl_6.6H_2O$ in isopropanol (prepared by dissolving 1 g of $H_2PtCl_6.6H_2O$ in 50 ml of isopropanol) are added.

The reaction mixture is heated to 85°–90° C. and, by operating under an inert gas atmosphere, 44 g (0.33 mol) is added of diethoxy-methyl-silane.

The reaction mixture is maintained stirred for 4 hours. The progressive disappearance of the reactants is monitored by gas-chromatographic analysis.

At the end of the reaction, the mixture is distilled and the product (VIII), which has a boiling temperature of 135°–137° C. (under 0.1 $mm_{Hg}$) is obtained with a yield of 70%.

EXAMPLE 12

Preparation of Compound (XI)

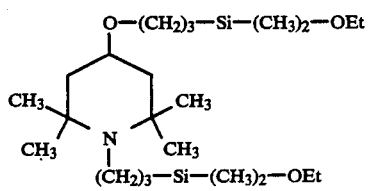

To a flask of 200 ml of capacity, equipped with thermometer, dropping funnel and bubble condenser, 23.8 g (0.1 mol) of compound (XVI), prepared as disclosed in Example 4, is charged, in the presence of 0.5 ml of a solution at 2% by weight of $H_2PtCl_6.6H_2O$ in isopropanol. The reaction mixture is heated to 85°–90° C. and 20.8 g (0.2 mol) of dimethyl-ethoxy-silane is added dropwise.

The reaction mixture is maintained stirred at 90° C. for 4 hours, and at the end of this time, it is distilled.

The product (XI), which has a boiling temperature of 190°–192° C. (under 0.2 $mm_{Hg}$) is obtained with a yield of 75%.

EXAMPLE 13

Preparation of Compound (XXVII)

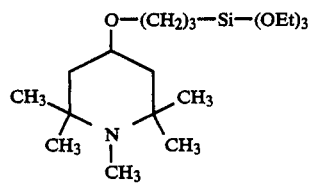

The process is carried out as disclosed in Example 11, but using triethoxysilane instead of methyl-diethoxysilane.

The product (XXVII) has a boiling temperature of 152° C. (under 0.2 $mm_{Hg}$).

EXAMPLE 14

Preparation of Compound (XXVIII)

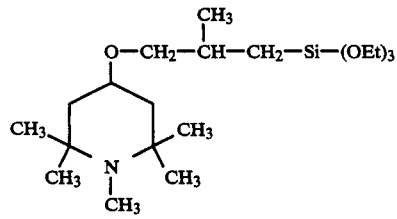

67.5 g (0.3 mol) of compound (XXV), prepared as disclosed in Example 6, is mixed with 0.4 ml of a solution containing $H_2PtCl_6$ in isopropanol (1 g of $H_2PtCl_6.6H_2O$ in 50 ml of isopropanol), and the resulting mixture is heated to the temperature of 85°–90° C. To this solution, 49.5 g (0.3 mol) of $HSi(OEt)_3$ is added dropwise.

The reaction mixture is then maintained stirred 8 hours at 85°–90° C., and is then distilled.

The product has a boiling temperature of 140°–145° C. (under 2.5 $mm_{Hg}$) and appears as a colourless viscous liquid.

EXAMPLE 15

Polymerization of the Ethoxy-Silyl-Derivatives

To a flask of 250 ml of capacity, equipped with anchor stirrer, and thermometer, surmounted by a distillation head, 0.1 mol of ethoxy-silyl-derivative, 0.3 mol of $H_2O$ and 0.005 mol of tin dibutyl-diacetate are charged.

The mixture is maintained 4 hours at the temperature of 90° C. In this way, ethyl alcohol which is formed during the hydrolysis reaction is distilled off.

After this time period, the distillation head is replaced by a Markusson-type extractor, 100 ml of toluene is added, and water is removed as an azeotrope, by increasing the temperature of the reaction mixture to 150° C.

The last traces of solvent are removed by operating under a vacuum of from 2 to 5 $mm_{Hg}$, at the above-indicated temperature.

The obtained products are very viscous liquids having an Mn comprised within the range of from 5000 to 8000.

In this way, the following polymers were prepared:

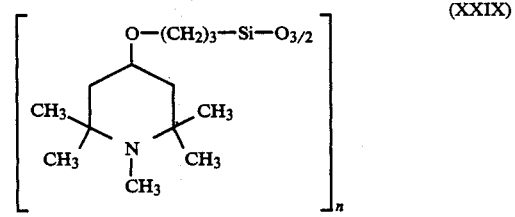

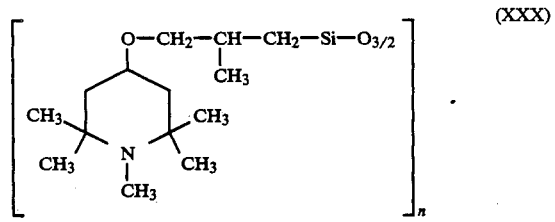

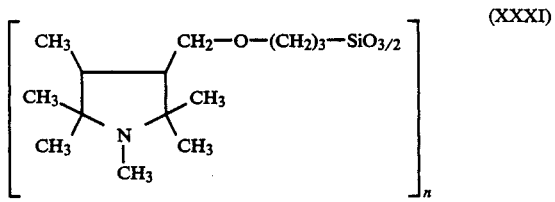

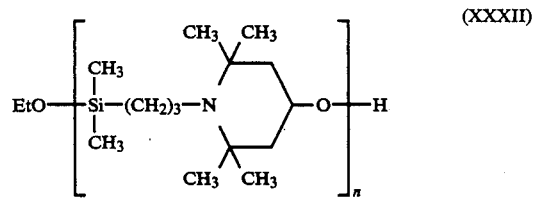

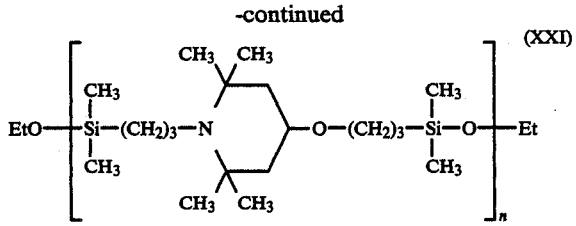

(XXI)

EXAMPLE 16

Copolymerization of the Ethoxy-Silyl-Derivatives With Glycols

To a flask of 250 cc of capacity, equipped with anchor stirrer, thermometer and distillation head, 0.1 mol of ethoxy-silyl-derivative, 0.1 mol of glycol, 100 cc of xylene and finally 1 mol of CH$_3$ONa were charged.

The reaction temperature is then slowly increased up to 130° C., with the ethyl alcohol arising from the polymerization reaction being distilled.

After 5 hours, the reaction solvent begins to be removed (the last traces are removed at a kettle temperature of 160° C. under a vacuum of 5 mm$_{Hg}$).

At room temperature, the products are viscous liquids having an Mn comprised within the range of from 5000 to 7000.

According to this synthesis methodology, the following polymers were obtained:

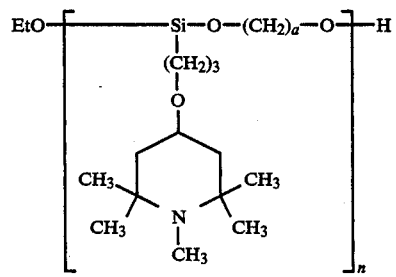

for a = 4   polymer (XXXIII)
for a = 6   polymer (XXXIV)
for a = 8   polymer (XXXV)

EXAMPLE 17

The products XXI, XXIX, XXX, XXXIV, XXXV, prepared as disclosed in the preceding Examples, were added to a polypropylene of Moplen FLF20 type (MFI$_{21.6}$$^{230°}$ $^{C.}$=9.2) containing 0.05% by weight of a phenolic antioxidant (BHT) and 0.05% by weight of a phosphite antioxidant (Sandostab PEPQ).

The operating procedure was as follows:

To a flask of 3 l of capacity, 400 g of polypropylene, 400 ml of hexane and 1 g of additive dissolved in 50 ml of hexane are added.

The mixture is stirred for 30 minutes, and at the end of this time the solvent is distilled off.

The last traces of solvents are removed by heating the polymer at 55° C. for 1 hour, under the pressure of 20 mm$_{Hg}$.

The so-obtained polymer granules were extruded in order to obtain a film from a flat head of approximately 60 mm of thickness, using a small laboratory extruder of Brabender type, equipped with a flat head.

The operating conditions were as follows:

Screw revolution speed: 70 rpm.
Temperature profile: 175°-200°-210°-220°-220° C.

For comparative purposes, also polypropylenes were extruded, which only contained the process stabilizers: BHT (0.05% by weight) and Sandostab PEPQ (0.05% by weight).

Furthermore, a polypropylene was extruded, which contained the process stabilizers in the above-detailed amount, and to which a HALS commercial product, Tinuvin 622, had been added, in the amount of 0.25% by weight relatively to the polymer.

The so-obtained films were submitted to irradiation with UV light, using an Atlas type UVCON equipment, operating under the following conditions:

| | |
|---|---|
| Black panel temperature | 55° C. |
| Humidity | 50% |
| Cycle | full light |

The characteristic which was checked is the disintegration time of the exposed samples.

The results are reported in the following Table:

TABLE 1

| Product | Disintegration Time (h) |
|---|---|
| PP* | 40 |
| PP + Tinuvin 622 | 380 |
| PP + (XXI) | 425 |
| PP + (XXIX) | 450 |
| PP + (XXX) | 400 |
| PP + (XXXIV) | 350 |
| PP + (XXXV) | 390 |

*PP = polypropylene

Furthermore, on polypropylenes containing 0.25% by weight of additives, the MFI$_{2.16}$ and the yellow index after 7 passages through the Brabender extruder, equipped with nozzle, and used under the same conditions as hereinabove reported, were measured.

The results are reported in the following Table:

TABLE 2

| Product | MFI | YI |
|---|---|---|
| PP | >30 | >15 |
| PP + (XXI) | 12.5 | 6.1 |
| PP + (XXIX) | 12.3 | 6 |
| PP + (XXX) | 10.5 | 4.3 |
| PP + (XXXI) | 11.7 | 4.7 |
| PP + (XXXII) | 26.0 | 9.4 |
| PP + (XXXIV) | 15 | 6.8 |
| PP + (XXXV) | 18 | 7 |

EXAMPLE 18

40 g of a hydroxylated acrylic resin having an equivalent weight, referred to the hydroxy group, of 1,200 (OH content=approx. 1.5%) is blended with 10 g of a polyfunctional aliphatic isocyanate having an equivalent weight, referred to isocyanate, of 324 (NCO content=approx. 13%).

To this blend, 0.25 g of products (VIII), (IX), (XXVII), (XXVIII), (XI), prepared as disclosed in the preceding Examples, and 50 ml of xylene are added.

The blend is then spread on a PVC support, and after allowing the solvent to evaporate at room temperature for a 5-day time, a film of 50 μm of thickness is obtained.

The so-obtained film is submitted to irradiation with UV light, using an ATLAS type WOM equipment, under the following operating conditions:

| | |
|---|---|
| Black panel temperature | 50° C. |
| Relative humidity | 50% |
| Cycle | full light |

For comparative purposes, specimens were prepared, which did not contain any additives, and specimens to which 0.5% by weight of Tinuvin 622, or 0.5% by weight of Tinuvin 292 was added.

On all of the films submitted to UV light, the disintegration times and the yellow indexes after 400 hours and 1000 hours of exposure in WOM were measured.

The following results were obtained:

TABLE 3

| PRODUCT | YI 400 h | YI 1000 h | Disintegration Time |
|---|---|---|---|
| Polyurethane film | 13 | | 350 |
| Polyurethane film + Tinuvin 622 | 2.1 | 8.5 | 1,200 |
| Polyurethane film + (IX) | 2.5 | 6.5 | 1,650 |
| Polyurethane film + (VIII) | 4 | 8.5 | 1,400 |
| Polyurethane film + (XXVII) | 3 | 5.5 | 1,500 |
| Polyurethane film + (XXVIII) | 5 | 6.5 | 1,500 |
| Polyurethane film + (XI) | 3 | 3.5 | 1,800 |
| Polyurethane film + Tinuvin 292 | 2 | 6 | 1,500 |

We claim:

1. Reactive stabilizer compounds containing a 2,2,6,6-tetramethylpiperidine group, a 2,2,6,6-tetramethylmorpholine group, or a 2,2,5,5-tetramethylpyrrolidine group, said groups bearing at least one silicic function hydrolyzable into silanol, linked by a silicon-carbon link, said stabilizer compounds having the following formulas:

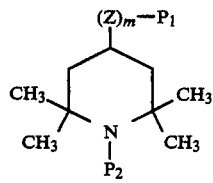

(IV)

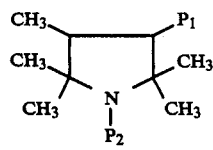

(V)

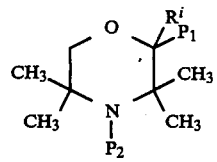

(VI)

wherein:
m is 0 or 1;
$R^i$ is H or $CH_3$;
Z is a group selected from

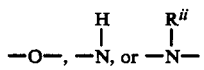

wherein $R^{ii}$ is a straight or branched alkyl radical containing from 1 to 5 carbon atoms;

wherein $P_1$, $P_2$ or both $P_1$ and $P_2$ are radicals having the formula:

(VII)

wherein R is a straight or branched alkylenic radical containing from 1 to 10 carbon atoms, or

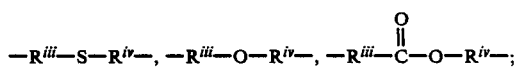

wherein $R^{iii}$ and $R^{iv}$ are straight or branched alkylene radicals containing from 2 to 10 carbon atoms;

X is a straight or branched alkyl radical of from 1 to 5 carbon atoms;

Y is H, halogen, acyl-($C_{1-4}$)-oxy, alkyl-($C_{1-4}$)-oxy, amino, amino-oxy or silyl-oxy;

n is 1, 2, or 3; and in the situation where either $P_1$ or $P_2$ is a radical of formula (VIII), the other of $P_1$ or $P_2$ is
  (a) a straight or branched alkyl radical of from 1 to 10 carbon atoms; or
  (b) a phenyl or cycloaliphatic, alkyl-phenyl or alkyl-cycloaliphatic radical.

2. The compounds according to claim 1, wherein X is a methyl radical and Y is chlorine or an alky-($C_{1-2}$)-oxy.

3. The compounds according to claim 1, wherein the compounds are selected from the group consisting of:

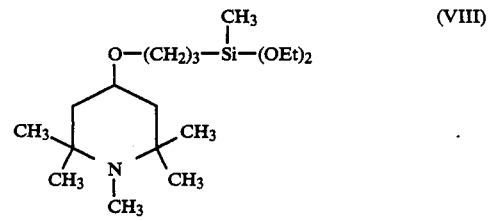

(VIII)

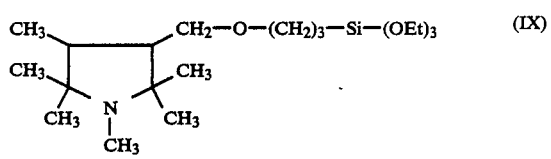

(IX)

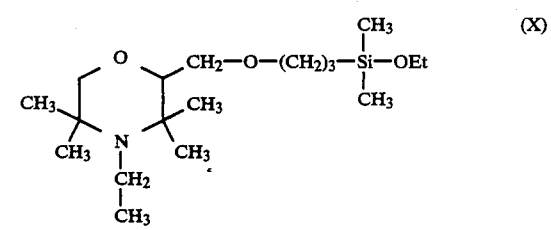

(X)

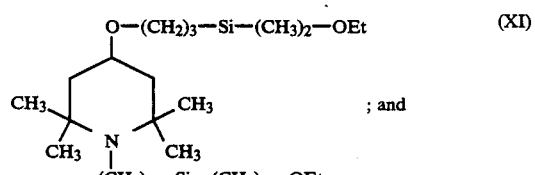

(XI)

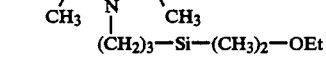

; and

-continued

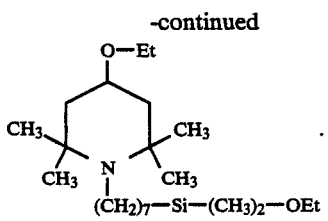

(XII)

4. A process for preparing the reactive stabilizer compounds of claim 1 comprising: reacting a 2,2,6,6-tetramethyl-piperidine, a 2,2,6,6-tetramethyl-morpholine or a 2,2,3,5,5-pentamethylpyrrolidine, having on the ring a group having an alkylenic unsaturated bond, with a silylating agent.

5. A process for the preparation of the reactive stabilizer compounds of claim 1 comprising: reacting a 2,2,6,6-tetramethyl-piperidine, a 2,2,6,6-tetramethyl-morpholine or a 2,2,3,5,5-pentamethylpyrrolidine, having on the nitrogen atom of the ring or on one of the carbon atoms of the ring, or on both the nitrogen atom and one of the carbon atoms on the ring, a group having an alkylenic unsaturated bone, with a silylating agent.

6. The process according to claim 4, wherein said silylating agent is

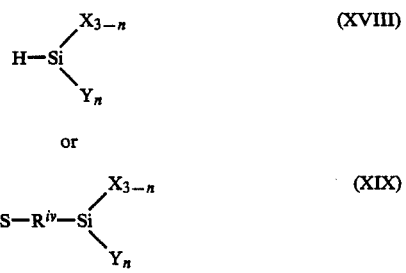

wherein $R^{iv}$, X, Y and n are as previously defined.

7. The process according to claim 6, wherein said silylating agent is methyl-diethoxy-silane, triethoxy-silane, dimethyl-chloro-silane, tetramethyl-disiloxane, or γ-mercaptopropyl-methoxy-silane.

8. The process according to claim 4, wherein the process is carried out at a temperature of from about 0° to about 200° C., in the presence of a catalyst selected from a metal catalyst, UV light and free-radical initiators, and for a time of from about 0.5 to about 10 hours.

9. The process according to claim 8, wherein the process is carried out at a temperature of from about room temperature up to about 120° C., with said catalyst consisting of a platinum compound, or of a platinum complex with olefins, in an amount of from 1 to 200 parts per million parts in the reaction medium, in the presence of an inert organic solvent selected from aliphatic, cycloaliphatic or aromatic hydrocarbons, and ethers.

10. Stabilized polymeric composition comprising: an organic polymer and an effective amount of a stabilizer product resulting from hydrolysis and resinification of the reactive stabilizer compound of claim 1.

11. The composition according to claim 10, wherein said hydrolysis and resinification are carried out in the presence of a catalyst selected from zinc octanoate, lead naphthenate and tin dibutyl-laurate.

12. The composition according to claim 10, wherein said hydrolysis and resinification are carried out in the presence of a silicon paint.

13. The composition according to claim 10, wherein the hydrolysis and resinification of the reactive stabilizer compound occur spontaneously inside the organic polymer.

14. A stabilized polymeric composition comprising: an organic polymer and an effective amount of the reactive stabilizer compound according to claim 1, fixed onto a solid support containing surface hydroxy groups.

15. The composition according to claim 14, wherein said solid support is selected from diatomaceous earth, celite, silica gel, cement, glass and silico-aluminates.

16. The composition according to claim 15, wherein said silica is fumed silica.

17. A stabilized polymeric composition comprising: an organic polymer and an effective amount of a reactive stabilizer compound according to claim 1, chemically bonded to the polymer.

18. The composition according to claims 10, 11, 12, 13, 14, 15, 16 or 17, wherein the organic polymer is an ethylene, propylene or butadiene homopolymer.

19. The composition according to claim 18, wherein the organic polymer is ethylene homopolymer.

20. The composition according to claim 10, wherein there is present an amount of the stabilizer compound which supplies from about 0.003 to about 0.3% of active nitrogen.

21. The composition according to claim 20, wherein there is present the amount of the stabilizer compound sufficient to provide an amount of active nitrogen of from about 0.005 to about 0.023% by weight.

* * * * *